United States Patent [19]

Modarress

[11] Patent Number: 4,688,943
[45] Date of Patent: Aug. 25, 1987

[54] FLUID OPTICAL DENSITY (OPACITY) PROBE

[75] Inventor: Dariush Modarress, Rolling Hills Estates, Calif.

[73] Assignee: Spectron Development Laboratories, Inc., Costa Mesa, Calif.

[21] Appl. No.: 848,815

[22] Filed: Apr. 7, 1986

[51] Int. Cl.$^4$ .................. G01N 21/01; G01N 21/59
[52] U.S. Cl. .................................. 356/436; 250/575; 356/437; 356/438
[58] Field of Search .............. 356/435, 436, 437, 438, 356/439, 442; 250/564, 565, 575, 578

[56] References Cited

U.S. PATENT DOCUMENTS 4,017,193  4/1977  Loiterman ........................ 356/438
4,290,695  9/1981  Schmitt ............................ 356/442

*Primary Examiner*—Vincent P. McGraw
*Attorney, Agent, or Firm*—Blakely Sokoloff Taylor & Zafman

[57] ABSTRACT

An apparatus and method for determining the extinction of laser light through a fluid is disclosed. The fluid is passed in a conduit having a light transmissive window. A laser beam having intensity $I_1$ is passed through the window into the fluid. A prong shaped probe having first and second probe sections is disposed in the fluid flow. The first probe section includes a beamsplitter at a distance $d_1$ from the window for redirecting a portion of the beam onto a first photodiode array, to determine the beam intensity $I_2$. The remaining portion of the beam tranverses a distance $d_2$ and is directed through a prism onto a second photodiode array to determine its intensity $I_3$. Based on the intensities $I_1$, $I_2$ and $I_3$ and given $d_1$ and $d_2$, the extinction values $E_1$ and $E_2$ may be calculated. Fluid optical density may then be determined as a function of the extinction.

16 Claims, 2 Drawing Figures

FLUID OPTICAL DENSITY (OPACITY) PROBE

BACKGROUND OF THE INVENTION

1. Field of the Invention:

The present invention relates to the field of determining the optical density (opacity) of a fluid, and more particularly, the determination of light extinction in a fluid using laser light.

2. Art Background:

There has long been a need to measure the density of sprays, gas flows, planetary atmospheres, combustion processes and the like. Such measurements are useful in combustion and nozzle applications, fuel analysis, planetary studies, etc. A number of techniques employing laser light to determine the extinction of a gas flow, and thereby its optical density, have been developed. In one system, the fluid is passed through a tube or conduit having windows aligned across the fluid flow. A laser beam is directed through one window and into the fluid flow, exiting out of a second window. By examining the intensity of the exiting beam, and knowing the distance traversed, the optical fluid density may be determined by the extinction characteristics of the beam. One common problem which leads to inaccuracy in such prior art systems is particulate deposition on the window inside the conduit passing the fluid. The deposition of particulates on the interior surfaces of the windows alters the extinction characteristics of the laser light, thereby resulting in an artificially high optical fluid density determination.

As will be described, the present invention provides a unique fluid density probe for use in determining light extinction through a fluid independent of the transmission coefficient through the access windows.

SUMMARY OF THE INVENTION

An apparatus and method for determining the extinction of laser light through a fluid is disclosed. The fluid is passed in a conduit having a light transmissive window. A laser beam having intensity $I_1$ is passed through the window into the fluid. A prong shaped probe having first and second probe sections is disposed in the fluid flow. The first probe section includes a beamsplitter at a distance $d_1$ from the window for redirecting a portion of the beam onto a first photodiode array, to determine the beam intensity $I_2$. The remaining portion of the beam traverses a distance $d_2$ and is directed through a prism onto a second photodiode array to determine its intensity $I_3$. Based on the intensities $I_1$, $I_2$ and $I_3$ and given $d_1$ and $d_2$, the extinction values $E_1$ and $E_2$ may be calculated. Fluid optical density may then be determined as a function of the extinction.

DETAILED DESCRIPTION OF THE INVENTION

An optical fluid density probe is disclosed, having particular application in the measurement of laser light extinction through a fluid media for the determination of optical fluid density. In the following description for purposes of explanation, numerous details are set forth such as specific optical arrangements, angles, wavelengths, etc. in order to provide a thorough understanding of the present invention. However, it will be apparent to one skilled in the art that the invention may be practiced without these specific details. In other instances, well known components, structures and electrical processing means have not been described in detail in order not to obscure the present invention unnecessarily.

Figure 1:
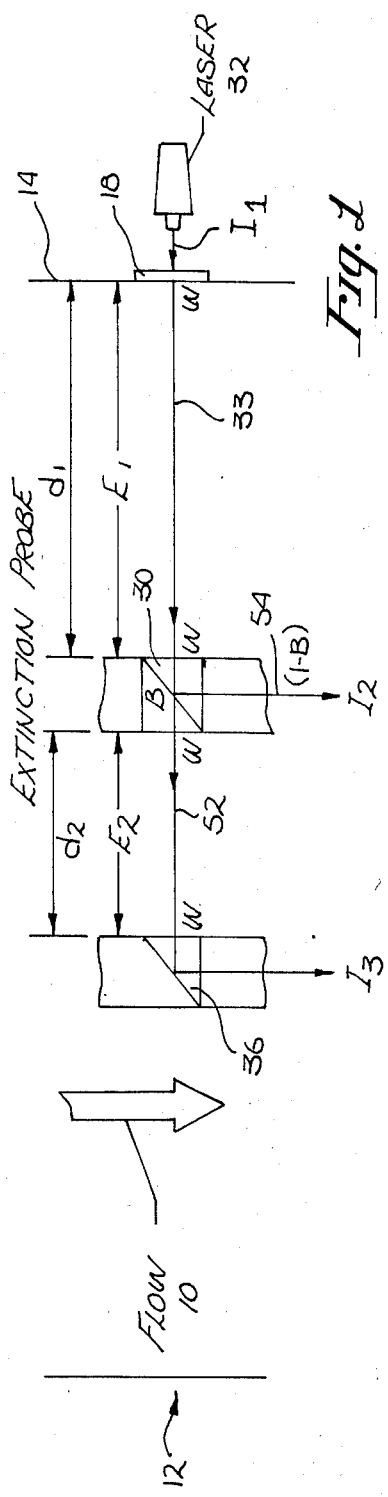
FIG. 1 is a schematic illustration of the present invention disposed within a conduit passing a fluid.

Referring to FIG. 1, a general optical arrangement of the present invention is disclosed in schematic form. In a typical application, a fluid flow 10 is passed through a conduit 12 which is bounded by a wall 14. In the case where conduit 12 is a tube or pipe, wall 14 simply comprises the wall of the tube or pipe, but, as will be apparent, the particular shape of the passage through which the flow 10 passes is not critical to the use of the present invention. For purposes of simplicity, in this Specification, wall 14 will be considered a boundary wall between flow 10 and the exterior environment. A window 18 is disposed through wall 14 to permit light to pass into conduit 12. Window 18 may comprise any one of a variety of optically transparent materials, such as glass, quartz and the like, and may be tailored to pass only desired wavelengths of light into conduit 12. In many prior art systems used to determine the extinction of a laser beam through a fluid media, the laser light is passed through window 18 into conduit 12 and is collected through a window disposed opposite the window 18 across the diameter of the conduit. The loss of intensity (I) of the initial beam passing through the window 18 and the flow 10 is used as basis for the determination of the optical density of the fluid as a function of light extinction.

Figure 2:
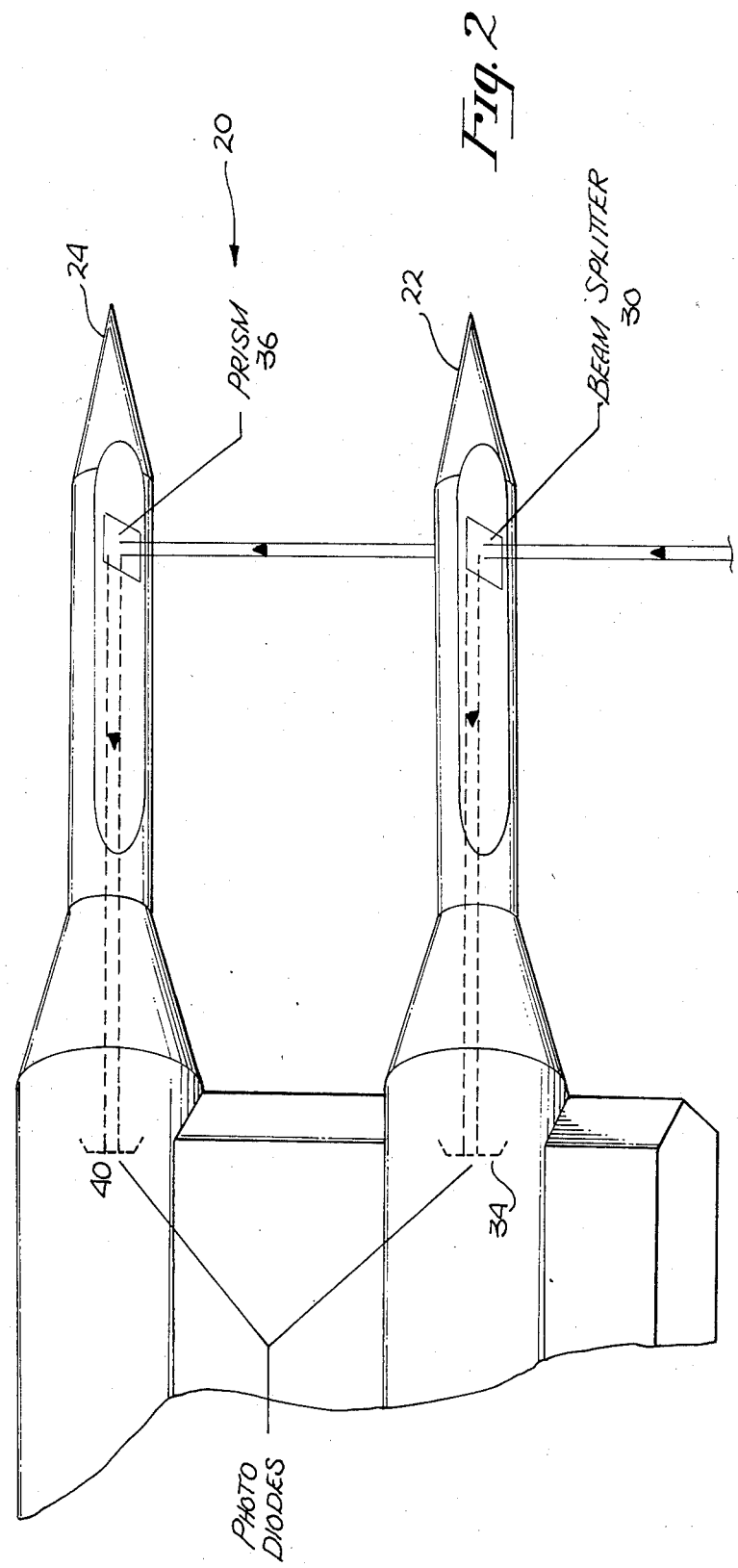
FIG. 2 is a partial cutaway section of the present invention illustrating its physical structure.

Referring briefly to FIG. 2, the present invention overcomes the disadvantages of prior art measurement systems by providing a probe, generally referred by the numeral 20 inside of conduit 12 and within the fluid flow 10. As illustrated in FIG. 2, probe 20 includes a first probe section 22 and a second probe section 24. Both sections 22 and 24 are shaped in a conical form in order to minimize disturbance of the flow 10 as it passes by the probe 20 in conduit 12. As further illustrated in FIGS. 1 and 2, probe 20 includes a beam splitter 30 disposed in optical alignment with window 18, such that light generated by laser 32 is passed through the window 18 onto the beam splitter 30. A portion of the light incident on beam splitter 30 is directed onto a photodiode 34, with the remaining light passing outward from section 22 onto a prism 36 disposed in section 24, as illustrated best in FIG. 2. Light incident on prism 36 is directed onto a second photodiode 40. The light directed on each respective photodiode 34 and 40 is converted into electrical signals proportional to the relative intensity of the light.

A historic problem in determining the extinction of laser light passing through a fluid flow is the errors resulting from particulate deposition on the windows (such as window 18 and the surfaces of beamsplitter 30 and prism 36) in the measurement system. The particulate deposition on the windows results in increased laser light extinction not necessarily indicative of the fluid density within the flow 10.

In operation, the present invention utilizes laser 32 to generate a laser beam 33 having an intensity $I_1$ which is passed through window 18 into conduit 12 and the fluid flow 10. Probe 20 is disposed at a known distance within flow 10, such that probe section 22 is situated a distance $d_1$ from window 18 and wall 14. Laser beam 33 directed through window 18 passes through that portion of flow 10 within the $d_1$, distance and experiences an extinction $E_1$ due to passage of the beam through that portion of the fluid flow. The beam 33 then passes onto beam splitter 30 where it is split (in the presently preferred embodiment by 50%) into two beams 52 and 54. Beam 54 is directed onto photodiode 34 which generate an electrical output proportional to the intensity of the beam passing through distance $d_1$ identified as $I_2$. The remaining beam 52 passes through probe section 22 and traverses distance $d_2$ between the probe sections 22 and 24, and thereby experiences additonal extinction $E_2$. Beam 52 then is directed onto prism 36 and onto photodiode 40 which generates an electrical output proportional to the intensity of beam 52 after traversing distance $d_2$, namely $I_3$.

Given the known distances $d_1$, $d_2$, and the intensities $I_1$, $I_2$, and $I_3$, the present invention permits determination of the extinction of light generated by laser 32 through passage of the fluid flow thereby permitting the determination of fluid density.

Extinction of the laser light (E) may be defined by the equation:

$$E = \frac{\text{Output of Laser}}{\text{Input Laser Power}}$$

The extinction of laser light due to deposition of particulates of the fluid flow on the glass surfaces, such as window 18, beam splitter 30 and prism 36 is assumed to be uniform and defined by the variable W. Moreover, in the present analysis, the ratio of the beam splitter 30 for transmission and reflection is defined by $\beta$. Thus, the following equations may be defined:

$$I_2/I_1 = E_1 \, W^{2*} (1-\beta) \quad \text{(A)}$$

$$I_3/I_1 = E_1 \, E_2 \, W^{4*} \beta \quad \text{(B)}$$

$$E_2 = (E_1)^{d1/d2} \quad \text{(C)}$$

Accordingly, the use of the apparatus of the present invention provides three equations (A), (B), (C) and three unknowns, namely $E_1$, $E_2$ and W. These equations may be solved using the following analysis:

$$I_2/I_1 = (E_2) \, W^2(1-\beta)$$
$$I_3/I_1 = (E_2) \, W^4 \beta$$
$$(I_2/I_1)^2 = (E_2) \, W^4(1-\beta)^2$$

$$\frac{(I_2/I_1)^2}{(I_3/I_1)} = (E_2)^{\frac{d1-d2}{d1}} \frac{(1-\beta)^2}{\beta}$$

$$E_2 = \frac{(I_2/I_1)^2}{(I_3/I_1)} \cdot \frac{\beta}{(1-\beta)^2} \; {}^{d2/(d1-d2)} (D) \text{ For } \beta \neq 0, \neq 1, \; d_2 \neq d_1$$

$$W = \frac{I_2/I_1}{1-\beta} (E_2)^{-d1/d2 \cdot \frac{1}{2}} \quad (E)$$

The use of the present invention in order to determine the distinction values of $E_1$, $E_2$ and W may be illustrated by the following example:

EXAMPLE

W=0.95, $d_1$=7 (units), $d_2$=5 (units)

$E_1$=0.868, $E_2$=0.904, $\beta$=0.5

$$E_2 = (E_1)^{5/7}$$

Measured values of $I_2/I_1$, $I_3/I_1$ $I_2/I_1 = (0.868)(0.95)^2(0.5) = (0.868)(0.904)(0.5) = 0.392$ $I_3/I_1 = (0.868)(0.904)(0.95)^4(0.5) = 0.319$ Solution Use these numbers to predict W, $E_1$, and $E_2$:

$$E_2 = \frac{(0.392)^2}{(0.319)} \cdot \frac{0.5^{\frac{5}{2}}}{(0.5)^2} = 0.903$$

$$W = \frac{0.392}{1 - 0.5} (0.903)^{-7/5 \cdot \frac{1}{2}} = 0.95$$

$$E_1 = (E_2)^{d1/d2} = 0.867$$

The present invention may also be used to measure the deposition on the window. The quantity W may be calculated directly from equations (D) and (E) if $I^1$, $I^2$, $I^3$, $\beta$, $d^1$ and $d^2$ are known:

$$W = \left(\frac{I_2/I_1}{1-\beta}\right)^{\frac{1}{2}} \frac{(I_2/I_1)^2}{(I_3/I_1)} \frac{\beta}{(1-\beta)^2} ^{\frac{-d1}{2(d1-d2)}}$$

The unique structure and method of the present invention overcomes the historic deficiencies of prior art devices for determining laser light extinction through a fluid flow. Although the present invention has been described with reference to FIGS. 1 and 2, it will be understood that the Figures are for illustration only and should not be taken as limitations upon the invention.

I claim:

1. An apparatus for determining the extinction of laser light through a fluid, comprising:
   laser generation means for generating a laser beam having an intensity $I_1$, said laser beam directed in a first direction into said fluid;
   first light directing means disposed in said fluid and in optical alignment with said laser beam for directing a portion of said laser beam in a second direction, said first light directing means located at a distance $d_1$ from the entry point of said laser beam into said fluid;
   second light directing means disposed in said fluid and in optical alignment with the remaining portion of said laser beam passing through said first light directing means, for directing said laser light in a third direction, said second light directing means located a distance $d_2$ from said first light directing means;
   sensing means in optical alignment with said laser beams directed in said second and third directions for determining the intensity of said beams, namely $I_2$ and $I_3$, respectively;
   calculation means coupled to said sensing means for determining the extinction of said laser beam over said distances $d_1$ and $d_2$, namely $E_1$ and $E_2$, respectively, as a function of $I_2$ and $I_3$;
   whereby the extinction of laser light through said fluid is determined.

2. The apparatus as defined by claim 1, wherein said fluid is passed through a conduit having a light transmissive window to permit said laser beam to pass into said fluid and onto said first light directing means.

3. The apparatus as defined by claim 2, wherein said first light directing means comprises a beamsplitter having a transmission/reflection ratio of $\beta$.

4. The apparatus of claim 3, wherein W is equal to the extinction of said laser light due to deposition of said fluid on said light transmissive window and said first and second light directing means.

5. The apparatus of claim 4, wherein the ratio of intensity is described as:

$$I_2/I_1 = E_1 \, W^2 * (1-\beta)$$

$$I_3/I_1 = E_1 \, E_2 \, W^4 * \beta$$

6. The apparatus of claim 4, wherein said extinction $E_2$ is described by:

$$E_2 = (E_1)^{d2/d1}$$

7. The apparatus of claim 6, wherein $E_2$ is described as:

$$E_2 = \frac{(I_2/I_1)^2}{(I_3/I_1)} \cdot \frac{\beta}{(1-\beta)^2}^{\frac{d2}{d1-d2}}$$

and $$W = \frac{I_2/I_1}{1-\beta} (E_2)^{-d1/d2\frac{1}{2}}$$

8. The apparatus of claim 4, wherein W is described as:

$$W = \left(\frac{I_2/I_1}{1-\beta}\right)^{\frac{1}{2}} \frac{(I_2/I_1)^2}{(I_3/I_1)} \frac{\beta}{(1-\beta)^2}^{\frac{-d1}{2(d1-d2)}}$$

9. A method for determining the extinction of laser light through a fluid comprising the steps of:
   generating a laser beam having an intensity $I_1$, said beam directed in a first direction into said fluid;
   at a distance $d_1$ from the entry point of said beam into said fluid directing a portion of said laser beam in a second direction;
   at a distance $d_2$ from the end point of $d_1$ directing the remaining portion of said laser beam in a third direction;
   determining the intensity of said beam directed in said second and third directions, namely $I_2$ and $I_3$, respectively;
   calculating the extinction of said laser beam over said distances $d_1$ and $d_2$, namely $E_1$ and $E_2$, respectively, as a function of $I_1$ and $I_3$;
   whereby extinction of light through said fluid is determined.

10. The method as defined by claim 9, wherein said fluid is passed through a conduit having a light transmissive window to permit said laser beam to pass into said fluid and onto said first light directing means.

11. The method as defined by claim 10, wherein said first light directing means comprises a beamsplitter having a transmission/reflection ratio of $\beta$.

12. The method of claim 11, where W is equal to the extinction of said laser light due to deposition of said fluid on said light transmissive window and said first and second light directing means.

13. The method of claim 12, wherein the ration of intensity is described as:

$$I_2/I_1 = E_1 \, W^2 * (1-\beta)$$

$$I_3/I_1 = E_1 \, E_2 \, W^4 * \beta$$

14. The method of claim 13, wherein said extinction $E_2$ is described by:

$$E_2 = (E_1)^{d2/d1}$$

15. The method of claim 14, wherein $E_2$ is described as:

$$E_2 = \frac{(I_2/I_1)^2}{(I_3/I_1)} \cdot \frac{\beta}{(1-\beta)^2}^{\frac{d2}{d1-d2}}$$

and $$W = \frac{I_2/I_1}{1-\beta} (E_2)^{-d1/d2\frac{1}{2}}$$

16. The method of claim 12, wherein W is described as $$W = \left(\frac{I_2/I_1}{1-\beta}\right)^{\frac{1}{2}} \cdot \frac{(I_2/I_1)^2}{(I_3/I_1)} \frac{\beta}{(1-\beta)^2}^{\frac{-d1}{2(d1-d2)}}$$

* * * * *